United States Patent
Nguyen et al.

(10) Patent No.: US 11,426,570 B2
(45) Date of Patent: Aug. 30, 2022

(54) CORE-SHELL MICRONEEDLE PLATFORM FOR TRANSDERMAL AND PULSATILE DRUG/VACCINE DELIVERY AND METHOD OF MANUFACTURING THE SAME

(71) Applicant: University of Connecticut, Farmington, CT (US)

(72) Inventors: Thanh D. Nguyen, Vernon, CT (US); Khanh Tran, Farmington, CT (US)

(73) Assignee: University of Connecticut, Farmington, CT (US)

( * ) Notice: Subject to any disclaimer, the term of this patent is extended or adjusted under 35 U.S.C. 154(b) by 516 days.

(21) Appl. No.: 16/293,588

(22) Filed: Mar. 5, 2019

(65) Prior Publication Data

US 2019/0269895 A1 Sep. 5, 2019

Related U.S. Application Data

(60) Provisional application No. 62/638,758, filed on Mar. 5, 2018.

(51) Int. Cl.
*A61M 37/00* (2006.01)
*A61B 17/20* (2006.01)
(Continued)

(52) U.S. Cl.
CPC ....... *A61M 37/0015* (2013.01); *A61B 17/205* (2013.01); *B29C 39/006* (2013.01);
(Continued)

(58) Field of Classification Search
CPC ..... B29C 39/003; B29C 39/006; B29C 39/02; B29C 39/026; B29C 39/028; B29C 39/04; B29C 65/02; B29C 43/003; B29C 43/02; B29C 43/021; B29C 43/027; B29C 43/04; B29C 43/20; B29C 43/203; B29C 43/32;
(Continued)

(56) References Cited

U.S. PATENT DOCUMENTS

| 5,891,191 A | 4/1999 | Stinson |
| 8,162,901 B2 | 4/2012 | Gonnelli et al. |

(Continued)

FOREIGN PATENT DOCUMENTS

| WO | 2006057987 A1 | 6/2006 |
| WO | 2008085904 A1 | 7/2008 |

(Continued)

OTHER PUBLICATIONS

European Patent Office Partial Search Report for Application No. 19764864 dated Dec. 21, 2021 (12 pages).
(Continued)

*Primary Examiner* — Atul P. Khare
(74) *Attorney, Agent, or Firm* — Michael Best & Friedrich LLP

(57) ABSTRACT

A core-shell microneedle system and a method of manufacturing the microneedle system provides a pulsatile drug delivery system which is programmed to release drugs/vaccines at predictable times using biodegradable polymers and with controllable dosages. This microneedle system can be fully embedded into the skin and then release drugs/vaccines as sharp bursts in a timely manner, similar to multiple bolus injections.

13 Claims, 7 Drawing Sheets

(51) Int. Cl.
| | |
|---|---|
| B29C 41/00 | (2006.01) |
| B29C 43/00 | (2006.01) |
| B29C 65/02 | (2006.01) |
| B29C 43/32 | (2006.01) |
| B29C 43/02 | (2006.01) |
| B29C 39/00 | (2006.01) |
| B29C 39/02 | (2006.01) |

(52) U.S. Cl.
CPC .......... *B29C 39/026* (2013.01); *B29C 41/003* (2013.01); *B29C 43/003* (2013.01); *B29C 43/021* (2013.01); *B29C 43/32* (2013.01); *B29C 65/02* (2013.01); *A61M 2037/003* (2013.01); *A61M 2037/0023* (2013.01); *A61M 2037/0046* (2013.01); *A61M 2037/0053* (2013.01); *A61M 2037/0061* (2013.01); *B29C 43/02* (2013.01)

(58) Field of Classification Search
CPC ...... B29C 2043/026; B29C 2043/3205; A61M 2037/0053
USPC .................. 264/241, 248, 250, 310, 311
See application file for complete search history.

(56) References Cited

U.S. PATENT DOCUMENTS

| | | | |
|---|---|---|---|
| 8,301,262 | B2 | 10/2012 | Mi et al. |
| 8,708,966 | B2 | 4/2014 | Allen et al. |
| 9,381,680 | B2 | 7/2016 | Oh et al. |
| 9,846,091 | B2 | 12/2017 | Lu et al. |
| 10,632,653 | B2* | 4/2020 | Niitsu ............... B29C 59/022 |
| 2008/0269666 | A1 | 10/2008 | Wang et al. |
| 2009/0182306 | A1 | 7/2009 | Lee et al. |
| 2011/0028905 | A1* | 2/2011 | Takada ............. A61K 31/7048 604/180 |
| 2011/0230747 | A1 | 9/2011 | Rogers et al. |
| 2012/0197155 | A1 | 8/2012 | Mattes et al. |
| 2013/0005708 | A1 | 1/2013 | Lalwani |
| 2013/0140649 | A1 | 6/2013 | Rogers et al. |
| 2014/0005606 | A1* | 1/2014 | Chen ................ A61K 9/5036 604/173 |
| 2015/0165020 | A1 | 6/2015 | Jaklenec et al. |
| 2016/0005951 | A1 | 1/2016 | Yoshida et al. |
| 2016/0050750 | A1 | 2/2016 | Rogers et al. |
| 2016/0184571 | A1 | 6/2016 | Admati |
| 2016/0184595 | A1 | 6/2016 | Hossainy |
| 2016/0287668 | A1 | 10/2016 | Tankovich |
| 2017/0020402 | A1 | 1/2017 | Rogers et al. |
| 2017/0080196 | A1 | 3/2017 | Lee et al. |
| 2017/0179370 | A1 | 6/2017 | Kim et al. |
| 2017/0189660 | A1 | 7/2017 | Baek |
| 2017/0252546 | A1 | 9/2017 | Park et al. |
| 2017/0258738 | A1 | 9/2017 | DeMuth et al. |
| 2017/0268942 | A1 | 9/2017 | Pedder et al. |
| 2017/0368321 | A1* | 12/2017 | Baek ................. B29C 39/003 |
| 2019/0328285 | A1 | 10/2019 | Liu |
| 2020/0009767 | A1* | 1/2020 | Li ..................... B29C 39/24 |

FOREIGN PATENT DOCUMENTS

| | | | | |
|---|---|---|---|---|
| WO | 2012103257 | A2 | 8/2012 | |
| WO | WO 2017/011320 | A1 | 1/2017 | |
| WO | WO-2017003238 | A1* | 1/2017 | ............ A61L 31/14 |
| WO | WO-2019143293 | A1* | 7/2019 | ............ A61K 47/34 |

OTHER PUBLICATIONS

Zhang et al., "Piezoelectric polymer multilayer on flexible substrate for energy harvesting," IEEE Transactions on Ultrasonics, Ferroelectrics, and Frequency Control, 2013, 60(9):12013-2020.
Ramadan et al., "A review of piezoelectric polymers as functional materials for electromechanical transducers," Smart Materials and Structures 23, 2014, 033001.
Dagdeviren et al., "Recent progress in flexible and stretchable piezoelectric devices for mechanical energy harvesting, sensing and actuation," Extreme Mechanics Letters, 2016, 9(1):1269-281.
European Patent Office Extended Search Report for Application No. 18767093.0 dated Nov. 27, 2020 (13 pages).
Amini et al., "Bone tissue engineering: recent advances and challenges," Critical Reviews™ in Biomedical Engineering, 2012, 40,(5):363-408.
Anglen, "The clinical use of bone stimulators," Journal of the Southern Orthopaedic Association, 2002, 12, (2), 46-54.
Bauer et al., "Bone Graft Materials: An Overview of the Basic Science," Clinical orthopaedics and related research, 2000, 371, 10-27.
Bussemer et al., "Pulsatile drug-delivery systems," Crit Rev Ther Drug Syst., 2001, 18(5):433-458, Abstract.
Carpentier et al., "Clinical trial of blood-brain barrier disruption by pulsed ultrasound," Science translational medicine, 2016, 8(343):343re2, 9 pages.
Chen et al., "Fully embeddable chitosan microneedles as a sustained release depot for intradermal vaccination," Biomaterials, 2013, 34(12):3077-3086.
Chiappini et al., "Biodegradable silicon nanoneedles delivering nucleic acids intracellularly induce localized in vivo neovascularization," Nature Materials, 2015, 14:532-539.
Cohen et al., "Totally implanted direct current stimulator as treatment for a nonunion in the foot," The Journal of foot and ankle surgery: official publication of the American College of Foot and Ankle Surgeons, 1993, 32, (4), 375-381.
Csafeglobal, The Cost of a Broken Vaccine Cold Chain Part Two, Financial Cost. <http://csafeglobal.com/the-cost-of-a-broken-vaccine-cold-chain-part-two-financial-cost-1> Sep. 17, 2014, 3 pages.
Curry et al., "Biodegradable piezoelectric force sensor," PNAS, 2018, 115(5):909-914.
Dai et al., "Electrospun emodin polyvinylpyrrolidone blended nanofibrous membrane: a novel medicated biomaterial for drug delivery and accelerated wound healing," Journal of Materials Science: Materials in Medicine, 2012, 23(11):2709-2716.
Demiray, "Electro-mechanical remodelling of bones," International Journal of Engineering Science, 1983, 21, (9), 1117-1126.
Ferreira et al., "Bone Collagen Role in Piezoelectric Mediated Remineralization," Acta Microscopica, 2009, 18(3):278-286.
Glazner et al., "Cost of vaccine administration among pediatric practices," Pediatrics, 2009, 124(Supplement 5):S492-S498.
Graf et al., "In Stimulation of bone growth by implanted FEP electrets and PVDF piezoelectric films," Proceedings 5th International Symposium on Electrets (ISE 5), Heidelberg, 1985, pp. 813-818.
Habibovic, "Strategic directions in osteoinduction and biomimetics," Tissue Engineering Part A, 2017, 23, (23-24), 1295-1296.
Laurencin et al., "Bone graft substitutes," Expert Review of Medical Devices, 2006, 3(1):49-57.
Laurencin et al., "Regenerative engineering," Science translational medicine, 2012, 4(160):160ed9, 4 pages.
Laurencin et al., "Tissue engineering: orthopedic applications," Annual review of biomedical engineering, 1999, 1, (1), 19-46.
Madlon-Kay et al., "Too many shots? Parent, nurse, and physician attitudes toward multiple simultaneous childhood vaccinations," Archives of Family Medicine, 1994, 3(7):610-13.
McHugh et al., Fabrication of tillable microparticles and other complex 3D microstructures, Science, 2017, 357(6356):1138-1142.
McHugh et al., "Single-injection vaccines: Progress, challenges, and opportunities," Journal of Controlled Release, 2015, 219:596-609.
Meng et al., "A Hybrid Inductive-Ultrasonic Link for Wireless Power Transmission to Millimeter-Sized Biomedical Implats," IEEE Transactions on Circuits and Systems—II: Express Briefs, 2017, 64(10):1137-1141.
Narayanan et al., "Poly (lactic acid)-based biomaterials for orthopaedic regenerative engineering," Advanced drug delivery reviews, 2016, 107, 247-276.
Nguyen et al., "Piezoelectric nanoribbons for monitoring cellular deformations," Nature Nanotechnology, 2012, 7:587-593.

(56) References Cited

OTHER PUBLICATIONS

Poeggel et al., "Optical Fibre Pressure Sensors in Medical Applications," Sensors, 2015, 15(7):17115-17148.
Rolland et al., "Direct fabrication and harvesting of monodisperse, shape-specific nanobiomaterials," Journal of the American Chemical Society, 2005, 127(28):10096-10100.
Sanni et al., "Inductive and Ultrasonic Multi-Tier Interface for Low-Power, Deeply Implantable Medical Devices," IEEE Transactions on Biomedical Circuits and Systems, 2012, 6(4):297-308.
Shende et al., Micro to nanoneedles: a trend of modernized transepidermal drug delivery system, Artificial Cells, Nanomedicine, and Biotechnology, 2017, 8 pages.
Simonelli et al., "Dissolution rates of high energy polyvinylpyrrolidone (PVP)-sulfathiazole coprecipitates," Journal of pharmaceutical sciences, 1969, 58(5):538-549.
Soltman et al., "Inkjet-printed line morphologies and temperature control of the coffee ring effect," Langmuir, 2008, 24(5):2224-2231.
Sullivan et al., "Dissolving polymer microneedle patches for influenza vaccination," Nature medicine, 2010, 16(8):915-921.
Tanimoto et al., "Effect of helix inversion of poly(β-phenethyl l-aspartate) on macroscopic piezoelectricity," Japanese Journal of Applied Physics, 2014, 53(9S):09PC01.
Vaers, Vaccine Adverse Event Reporting System. <https://vaers.hhs.gov/data/index> webpage available as early as Oct. 9, 2009, 2 pages.
Xu et al., "Future of the particle replication in nonwetting templates (PR.INT) technology," Angewandte Chemie International Edition, 2013, 52(26):6580-6589.
Yu et al., "Oral fast-dissolving drug delivery membranes prepared from electrospun polyvinylpyrrolidone ultrafine fibers," Nanotechnology, 2009, 20(5):055104, 9 pages.
International Search Report and Written Opinion for Application No. PCT/US2019/020838 dated Jun. 26, 2019 (14 pages).
Ando et al., "Pressure-sensitive touch panel based on piezoelectric poly (l-lactic acid) film", 2013, Jpn. J. Appl. Phys. 52:09KD17.
Bello et al., "Development of a smart pump for monitoring and controlling intraocular pressure", Ann Biomed Eng 45:990-1002, 2017.
Bos et al., "Resorbable poly(L-lactide) plates and screws for the fixation of zygomatic fractures", 1987, J Oral Maxillofac Surg, 45:751-753.
Chee et al., "An investigation of array of piezoelectric transducer for raindrop energy harvesting application", 2016, IEEE Region Tenth Conference, pp. 3771-3774.
Lee et al., "Micromachined piezolectric force senors based on PZI thin films", 1996, IEEE Trans Ultrason Farroelectri Freq Control, 43:553-559.
Di Mario et al., "Drug-eluting bioabsorbable magnesium stent", 2004, J Interv Cardiol., 17:391-395.
Fukada, "New Piezoelectric polymers" 1998, Jpn J Appl Phys 37:2775-2780.
Ewald et al., "Monitoring of vital signs for long-term survival of mice under anesthesia", 2011, Cold Spring Harb Protoc. 2011:pdb.prot5563.
Guo et al., "Measurements of piezoelectric coefficient d33 of lead zirconate titanate thin films using a mini force hammer", 2013, J Vib Accoust, 135:011003.
Jayson et al, "Intra-articular pressure in rheumatoid arthritis of the knee 3. Pressure changes during joint use", Ann Rheum Dis, 1970, 29:401-408.
Kang et al., "Bioresorbable silicon electronic sensors for the brain", Nature, 2016, 530:71-76.
Liu et al., "Design and development of three-dimensional scaffolds for tissue engineering", 2007, Chem Eng Res Des, 85:1051-1064.
Maloney et al., "Intracranial pressure monitoring in acute liver failure: Institutional case series", 2016, Neurocrit Care 25:86-93.

Masamichi et al., "Film sensor device fabricated by a piezoelectric poly(L-lactic acid) film", 2012, Jpn J Appl Phys 51:09LD14.
Masamichi et al., "Pressure sensitive touch panel based on piezoelctric poly(L-lactic acid) film", 2013, Jpn J Appl Phys 52:09KD17.
Minary-Jolandan et al., "Nanoscale characterization of isolated individual type I collagen fibrils: Polarization and piezoelectricity", 2009, Nanotechnology 20:085706.
Nguyen et al., "Wafter-scale nanopatterning and translation into high-performance piezoelectric nanowires", 2010, Nano Lett 10: 4595-4599.
Nguyen, et al., "Bionics in tissue engineering" 2017, Tissue Engineering for Artifical Organs, pp. 677-669.
Qi et al., "Enhanced piezoelectricity and stretchability in energy harvesting devices fabricated from buckled PZT ribbons", 2011, Nano Lett 11:1331-1336.
Qi et al., "Stretchable piezoelectric nanoribbons for biocompatible energy harvesting", Stretchable Electrionics, pp. 111-139.
Ru et al., "Dominant B-form of poly(l-lactic acid) obtained directly from melt under shear and pressure fields", 2016, Macromolecules 49:3826-3837.
Saravanos et al., "Layerwise mechanics and finite element for the dynamic analysis of piezoelectric composite plates", 1997, Int J Solids Struct 34:359-378.
Sawano et al., "New design of actuator using shear piezoelectricity of a chiral polymer, and prototype device", 2010, Polym. Int. 59: 365-370.
Seol et al., "Hysteretic behavior of contact force response in triboelectric nanogenerator", 2017, Nano Energy 32:408-413.
Sinderby et al., "Diaphragm activation during exercise in chronic obstructive pulmonary disease", 2001, Am J Respir Crit Care Med, 163:1637-1641.
Syuhei et al., "Sensing using piezoelectric chiral polymer fiber", 2012, Jpn. J. Appl. Phys. 51:09LD16.
Tajitsu et al., "Microactuators with piezoelectric polylactic acid fibers—toward the realizaation of tweezers for biological cells", 2004, Ferroelectrics 304:195-200.
Talmor et al., "Mechanical ventilation guided by esophageal pressure in acute lung injury", N. Engl. J Med., 2008, 359, 2095-2104.
Xu et al., "Improvements of thermal property and crystallization behavior of PLLA based multiblock copolymer by forming sterocomplex with PDLA oligomer", 2006, Polymer (Guildf), 47:3922-3928.
Yoshida et al., "High piezoelectric performance of poly (lactic acid) film manufactured by solid state extrusion", 2014, Jpn. J. Appl. Phys. 53:09PC02.
Yoshida et al., "Piezolectric motion of multilayer film with alternate rows of optical isomers of chiral polymer film", 2011, Jpn J Appl Phys 50:09ND13.
Zheng et al., "Biodegradable triboelectric nongenerator as a lifetime designed implantable power source", 2016, Sci Adv 2:e1501478.
Zi et al., "Triboelectric-pyroelectric-piezoelectric hybrid cell for high-efficiency energy-harvesting and self-powered sensing", Adv Mater 27:2340-2347, 2015.
D'Lima et al. "Implantable sensor technology: measuring bone and joint biomechanics of daily life in vivo", Arthritis Reseasrch and Therapy, 2013, 15: 203.
Klosterhoff et al., "Implantable Sensors for Regenerative Medicine", Journal of Biomechanical Engineering, ASME Feb. 2017, vol. 139, 021009-1.
Boutry et al., "A sensitive and Biodegradable Pressure Sensor Array For Cardiovascular Monitoring", Advanced Materials, 27, 2015, pp. 6954-6961.
International Search Report and Written Opinion for Application No. PCT/US2018/022441 dated Aug. 1, 2018 (12 pages).
International Preliminary Report on Patentability for Application No. PCT/US2018/022441 dated Sep. 17, 2019 (10 pages).

* cited by examiner

CORE-SHELL MICRONEEDLE PLATFORM FOR TRANSDERMAL AND PULSATILE DRUG/VACCINE DELIVERY AND METHOD OF MANUFACTURING THE SAME

CROSS-REFERENCE TO RELATED APPLICATIONS

This application is a non-provisional of and claims the benefit of U.S. Provisional Patent Application No. 62/638,758, filed on Mar. 5, 2018, the contents of which are incorporated herein by reference.

BACKGROUND

Injections in conventional administration of vaccines are problematic. First, most of the vaccines are administered into children, who are needle-phobic. These painful injections could also cause infection and induce bad skin inflammatory reactions. Second and critically the injections require patients to memorize their vaccine schedules and bring their children to medical centers at multiple times. This is an immense obstacle for people who live in remote areas far away from medical centers. Millions of patients especially in developing countries currently have to walk tens of kilometers to bring their kids to medical centers multiple times when their children need vaccine shots. Therefore, patient accessibility is highly limited by the requirement of these multiple shots, leading to incomplete vaccination process, and the reoccurrence and spreading of deadly viral diseases. Third, in terms of cost, it is expensive to hire trained people/nurses to perform vaccine injections. Every year, about 10 million injections of vaccine are conducted for children under one year old (not including adults). As the price of administration is about $12/injection, it is about $120 million spent annually. This has not taken into account the waste of cold-chain vaccines (about $3 million a year per each state in the U.S.). The vaccine easily degrades during storage time between different shots and transportation processes. Finally, the injections produce millions of disposed sharp needles, producing a large amount of sharp hazardous biowaste. As such, these injections are a significant burden to patients, society, economics and environment. Consequently, there is a tremendous need to develop a single-administered painless and easy-to-use microneedle system with pulsatile release to replace conventional vaccine injections.

Microneedle patches have been explored and shown to exhibit advantages in transdermal delivery, however there have not been any reports on the use of this approach for single-administered multi-pulse delivery. Typically, current microneedles in which therapeutic agents are incorporated into the polymeric carriers only allow immediate or sustained releases. Another system like hollow microneedles even though provides a micro-infusing system, it requires an external drug reservoir on the skin or portable devices.

SEAL (StampED Assembly of polymer Layers) has demonstrated the concept of single-administered multi-pulse vaccine delivery. SEAL relies on a laborious manual process to remove scum/residual layers of polymer after molding steps and a slow process to fill drugs into polymeric carriers in serial (i.e., one by one). This filling struggles with instability of off-target jetting and severely suffers from the coffee-ring effect which results in drugs being deposited more on the edges of the drug micro-cores preventing a maximal loading efficiency (see FIG. 1).

SEAL has been shown to create different polymeric layers. However, the method results in a thick scum residual layer, requiring a manual, inconsistent and slow removal process (with scotch-tape and oxygen plasma). Using the so-called PRINT technology (Xu, J.; Wong, D. H.; Byrne, J. D.; Chen, K.; Bowerman, C.; DeSimone, J. M., Future of the particle replication in nonwetting templates (PR.INT) technology. Angewandte Chemie International Edition 2013, 52, (26), 6580-6589), researchers have shown that synthetic super-hydrophobic Teflon-like polymer can be employed to mold micro/nano particles without creating a scum layer. Yet, the polymer source is very limited and too costly while chemical synthesis is still required to obtain the final polymer resin.

Existing fabrication methods, although able to incorporate drugs with the microneedles, still struggle with major limitations. First, current fabrication methods have little-to-no control over microneedles internal structures to enable delayed pulsatile release. Due to such a limitation, available microneedles can only exhibit sustained release or immediately burst out drugs right after the needles are inserted into skin. Second, these microneedles are usually accompanied with a thick flashing/residual base layer, which potentially causes discomfort and skin irritation, making the needles not suitable for long-term skin integration.

SUMMARY

The core-shell microneedle system according to an embodiment provides a pulsatile drug delivery system which is programmed to release drugs/vaccines at predictable times using biodegradable polymers and with controllable dosages. This is the first microneedle system which would be fully embedded into the skin and then release drugs/vaccines as sharp bursts in a timely manner, similar to multiple bolus injections.

The fully-embedded coreshell microneedle is significantly less invasive compared to hypodermal/intramuscular injection of SEAL-particles. In terms of drug loading, the previous drug filling process is not only slow, laborious, and requires an expensive filling device but also struggles with instability of off-target jetting and severely suffers from the coffee-ring effect which results in drugs to be deposited more on the edges of the drug micro-cores, preventing a maximal loading efficiency (FIG. 1). Meanwhile, the new drug-loading and scum removing method do not suffer from such disadvantages and at the same time offer a high scalability The work includes two major innovations in terms of manufacturing technology and controlled-delivery drug-carrier. Although microneedle patches have been explored and shown to exhibit advantages in delivering and enhancing vaccine efficacy, there have not been any reports on the use of this approach for single-administered multi-pulse vaccine delivery. Herein, is disclosed novel core-shell microneedles which will be fully embedded into skin and release vaccines as sharp bursts in a predictable timely manner, similar to multiple bolus injections. The microneedles will not only allow for an easy, one-time self-administration of vaccine but also increase efficiency of the immunization since they target numerous antigen-presenting cells at the dermal layers. This is a tremendous benefit to solve the global problem of incomplete immunization while sparing antigen by boosting the vaccine activity.

Technology-wise, a highly innovative manufacturing process is disclosed that solves critical problems of the previously-reported SEAL method. (McHugh, K. J.; Nguyen, T.

D.; Linehan, A. R.; Yang, D.; Behrens, A. M.; Rose, S; Tochka, Z. L.; Tzeng, S. Y.; Norman, J. J.; Anselmo, A. C., Fabrication of fillable microparticles and other complex 3D microstructures. Science 2017, 357, (6356), 1138-1142). Embodiments of the manufacturing method described herein eliminates the presence of scum/residual layer through a facile procedure. A new drug-loading approach, which does not rely on the serial and slow filling process, is also described. Arrays of molded drug cones are simultaneously placed into arrays of the microneedles in a parallel and high throughput manner while at the same time, sealing the drug cores.

The use of an advanced manufacturing technology to create novel core-shell microneedles, which could perform timely pulsatile release to solve the critical problem of repetitive and painful injections in conventional vaccine-administrations, makes this work innovative.

This new manufacturing process creates novel core-shell microneedles which can be fully inserted inside the skin and programmed to deliver vaccines or drugs at different times, similar to multiple bolus injections. These microneedles will increase patient accessibility to the vaccine, fostering the goal of global immunization to eradicate, and prevent deadly infectious diseases. Moreover, the needles would also offer a platform technology to administer versatile drugs (e.g., growth hormone, allergic drugs, pain medicine, etc.) which require frequent injections.

The ability to control internal structures and load different materials into cores of other materials allows us to create 3D micro-structures with an extreme complexity, while sustaining an excellent resolution and fidelity of the structures via micro-molding processes. Such 3D complexes of bioerodible polymers without any potentially-toxic impurities offer important applications in the fields of controlled drug delivery, tissue engineering and medical devices. The microneedle system disclosed herein can significantly enhance the efficiency of vaccine delivery by combining the concept of dermal/skin delivery and pulsatile release which has not been achieved from currently available microneedle patches.

In one embodiment, the disclosure describes a pulsatile drug delivery system comprising a microneedle assembly including a plurality of microneedles filled with a therapeutic agent. The microneedles comprise biodegradable polymers, and the microneedle assembly is configured to release the therapeutic agent at predetermined times with a predetermined amount of the therapeutic agent while the microneedle assembly remains embedded in a patient.

In another embodiment, the disclosure provides a method of manufacturing a microneedle assembly. The method comprises generating a core microneedle assembly by filling a first silicone mold including a plurality of microneedle cavities with a copolymer, spinning the first silicone mold to remove a first scum layer of the copolymer on the first silicone mold, and generating a core in each of the copolymer-filled cavities. The method further comprises generating a therapeutic agent assembly by filling a plurality of cavities in a second silicone mold with a therapeutic agent, spinning the second silicone mold to remove a second scum layer of the therapeutic agent, and removing the molded therapeutic agent from the second mold and transferring the molded therapeutic agent to a substrate. The method further comprises aligning the therapeutic agent assembly with the core microneedle assembly to thereby fill the cores in the core microneedle assembly with the therapeutic agent.

Other aspects of the invention will become apparent by consideration of the detailed description and accompanying drawings.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

A drug delivery system according to an embodiment of the present disclosure provides a one-time administration of one or more therapeutic agents of one or more dosages which are programmed to release at predictable time points. For example, degradation of the polymeric shell of the microneedles provides for release of the therapeutic agent. The drug delivery system can replace multiple bolus injections of many therapeutic agents, especially vaccines which require initial dose and multiple boosters.

The drug delivery system includes coreshell microneedles that overcome the above-noted SEAL limitations in fabrication, provide a minimally invasive approach, and allows for self-administration. Importantly, for vaccine delivery, the needles pierce into the dermis layer of the skin where there is a substantial number of immune cells, thereby significantly enhancing immune response. Microneedles are, therefore, an appealing delivery approach to enable one-time, painless, and effective administration of vaccines to replace multiple injections in the conventional immunization process. The microneedles are fabricated from FDA approved materials (e.g., Poly(D,L-lactide-co-glycolide) (PLGA), poly-lactide acid (PLA)) that are commonly used for drug delivery, medical devices, etc.

Figure 1:
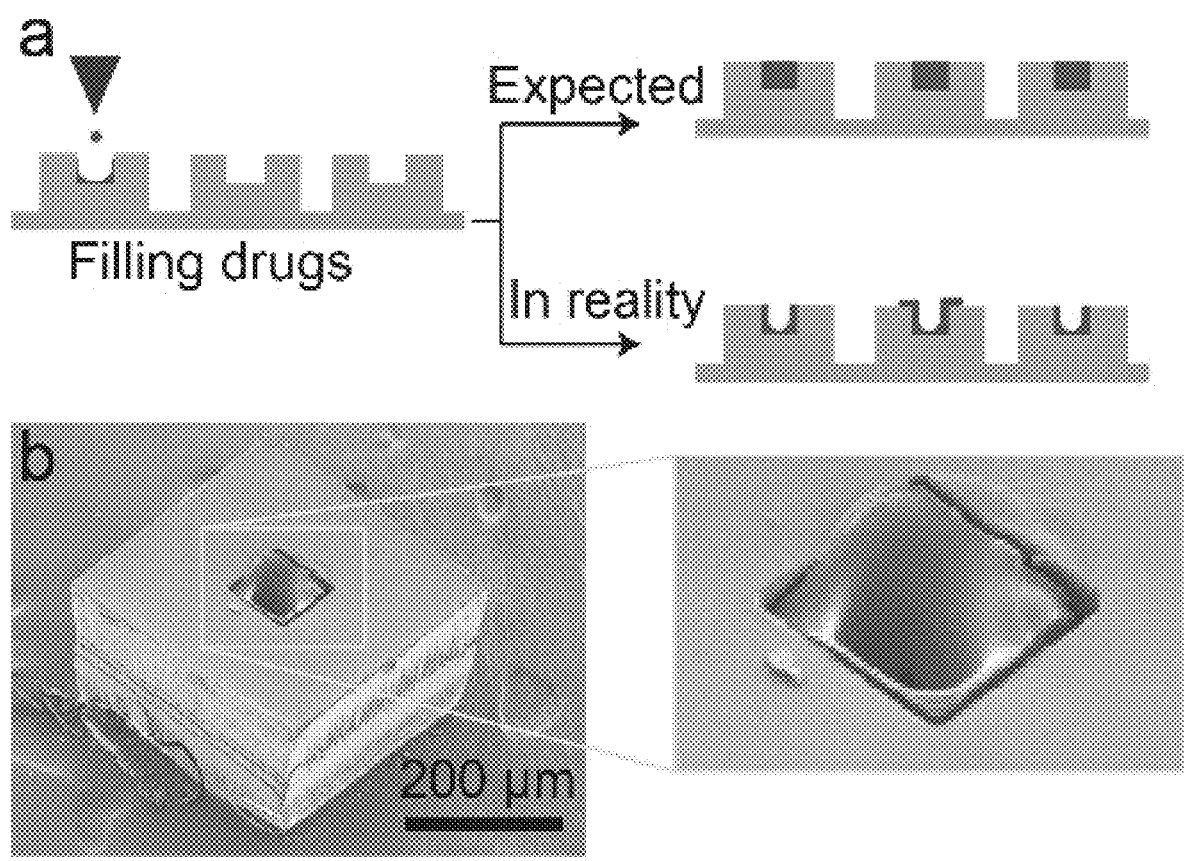
FIG. 1 illustrates current problems with the serial and slow filling process in SEAL. Schematic describes the problem (at a). Coffee-ring effect from solution-filling (at b).
Figure 2:
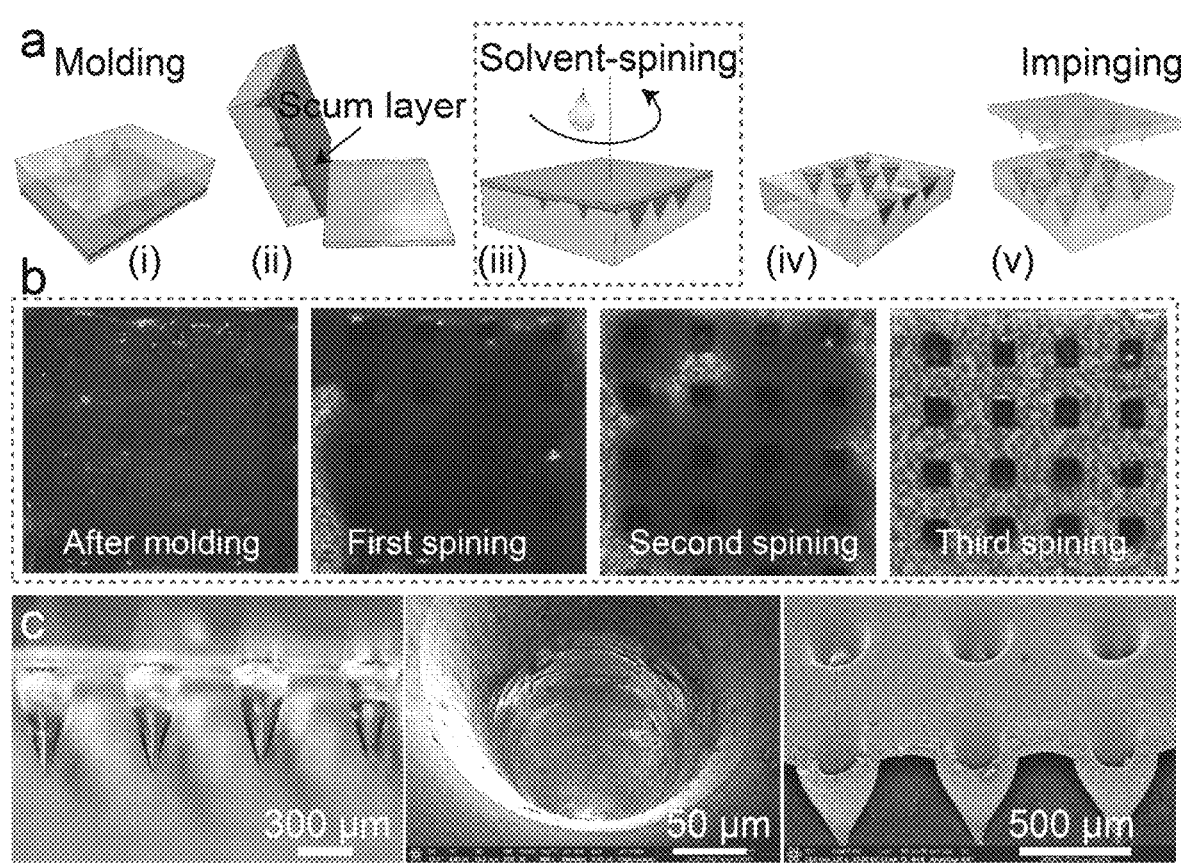
FIG. 2 illustrates fabrication of microneedles with empty cores (at a); optical images show step-by-step removal of scum layer by solvent-spinning (at b); and preliminary data on the fabricated microneedles with empty cores (at c).

The master structures for the microneedles are fabricated using a 3D laser lithography system (Nanoscribe GmbH). Inverse molds comprising silicone (Polydimethylsiloxane ("PDMS")) are made by pouring PDMS solution over the master structure and curing at 60° C. for 3 hours. A new process is employed which only relies on common PDMS molds to eliminate the scum layer. FIG. 2 (at a) describes the fabrication process in which a needle mold of PDMS is pressed onto a hot Poly(D,L-lactide-co-glycolide) ("PLGA") (i). The PLGA is trapped inside the cavity of the mold, which is then separated from the substrate (ii). The released mold has a significant scum layer which needs to be removed to create free-standing and fully-embeddable needles. To achieve this, the PDMS mold (using spin-coater) is spun and solvent (e.g., acetone, dimethyl sulfoxide ("DMSO")) or water (to remove hydrophilic drug) is gently dropped on top to remove the scum layer (iv). This spinning process can be repeated until the scum layer is completely removed.

FIG. 2 (at b) shows preliminary data in removing the scum layer of molded PLGA in PDMS. A high molecular weight PLGA (MW~200 kDa and LA:GA=85:15) is mixed with a red dye for visualization. This PLGA was molded into small slabs inside a PDMS mold. A thick scum layer was present after the molding process but after a few spinning steps with acetone, the scum layer was completely removed. In addition to scum layer removal, microneedles with conical empty cores were created by this impinging process, as seen in FIG. 2 (at c). In the final step (v), another mold is impinged onto the needle, trapped inside the PDMS mold, to create dimples or cores which are used to contain therapeutic agents.

Figure 3:
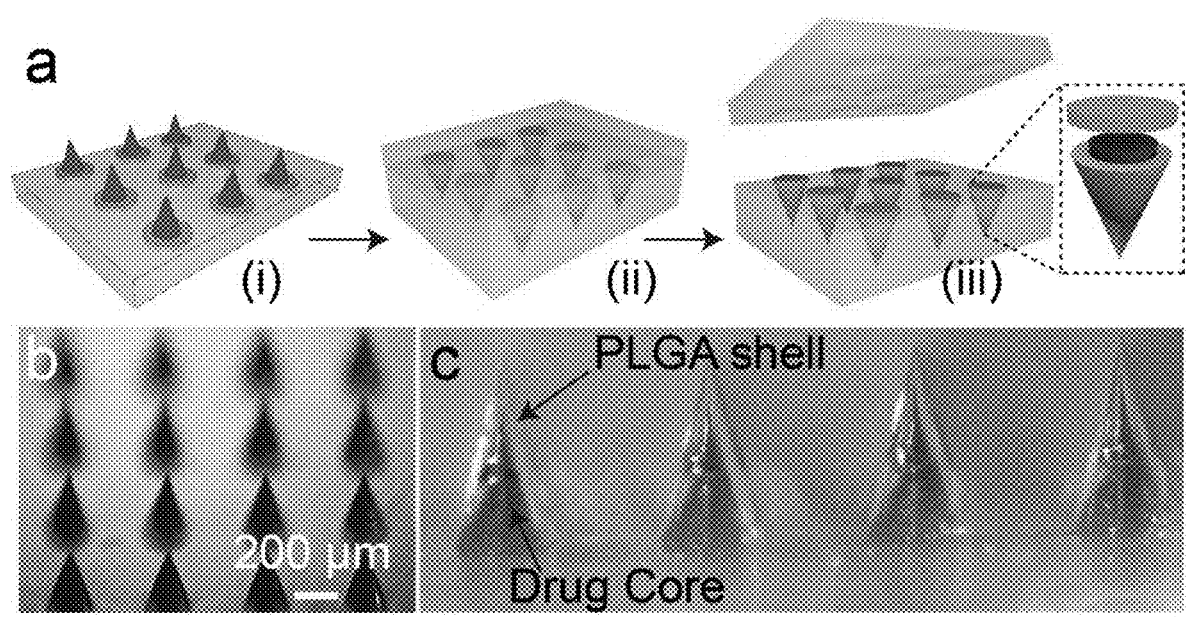
FIG. 3 illustrates microneedles being loaded and sealed with drugs in a single step. Diagram showing the process (at a). An image that shows micro-molded drug/vaccine cores with red dye and no scum-layer (at b). An image that shows preliminary data on the fabricated core-shell microneedles (at c).

SEAL relies on a slow and ineffective process to fill therapeutic agents into tiny micro-cores. Herein, a novel loading process to solve that problem is disclosed. First, a PDMS stamp is used to mold the drug/vaccine of interest into conical shapes, mixed with a polymeric carrier. Depending on the therapeutic agents, suitable polymeric solutions are selected. Some common polymers are Polyvinylpyrrolidone ("PVP"), Polyvinyl alcohol ("PVA"), Polyethylene glycol ("PEG"), (Hydroxypropyl)methyl cellulose ("HPMC"). Formulations can be made to improve the stability of drugs/vaccines. This disclosure demonstrates the use of PVP, the commonly used polymer for medical devices and implants such as wound dressings and drug tablets. The polymer is highly water-soluble, facilitating an immediate release of the encapsulated drugs with sharp release bursts after contact with water. The molding is similar to the process in FIG. 2 (at a, steps (i)-(ii)) but occurs at room/low temperatures to avoid damage to the vaccine. The scum layer is removed by spinning water on top of the PDMS stamp, containing the molded drug cones. The drug-PVP cores are then aligned and transferred on a cap-layer of PLGA, which has been molded and trapped inside another PDMS mold (see FIG. 3 (at a, (i)). Finally, this cap layer is aligned and pressed on the microneedle shell under a slightly-increased temperature to simultaneously load drugs and seal the microneedles, as seen in FIG. 3 (at a, (ii)-(iii)). The concentration of drugs in PVP can be easily tailored and the volume of the molded drug-core (FIG. 3 (at b)) can be approximated for one of the needle cores, allowing a maximal loading efficiency. The loading and sealing process was employed to successfully create the core-shell microneedles, as seen in FIG. 3 (at c). This process is further described with reference to FIGS. 5-6.

Figure 4:
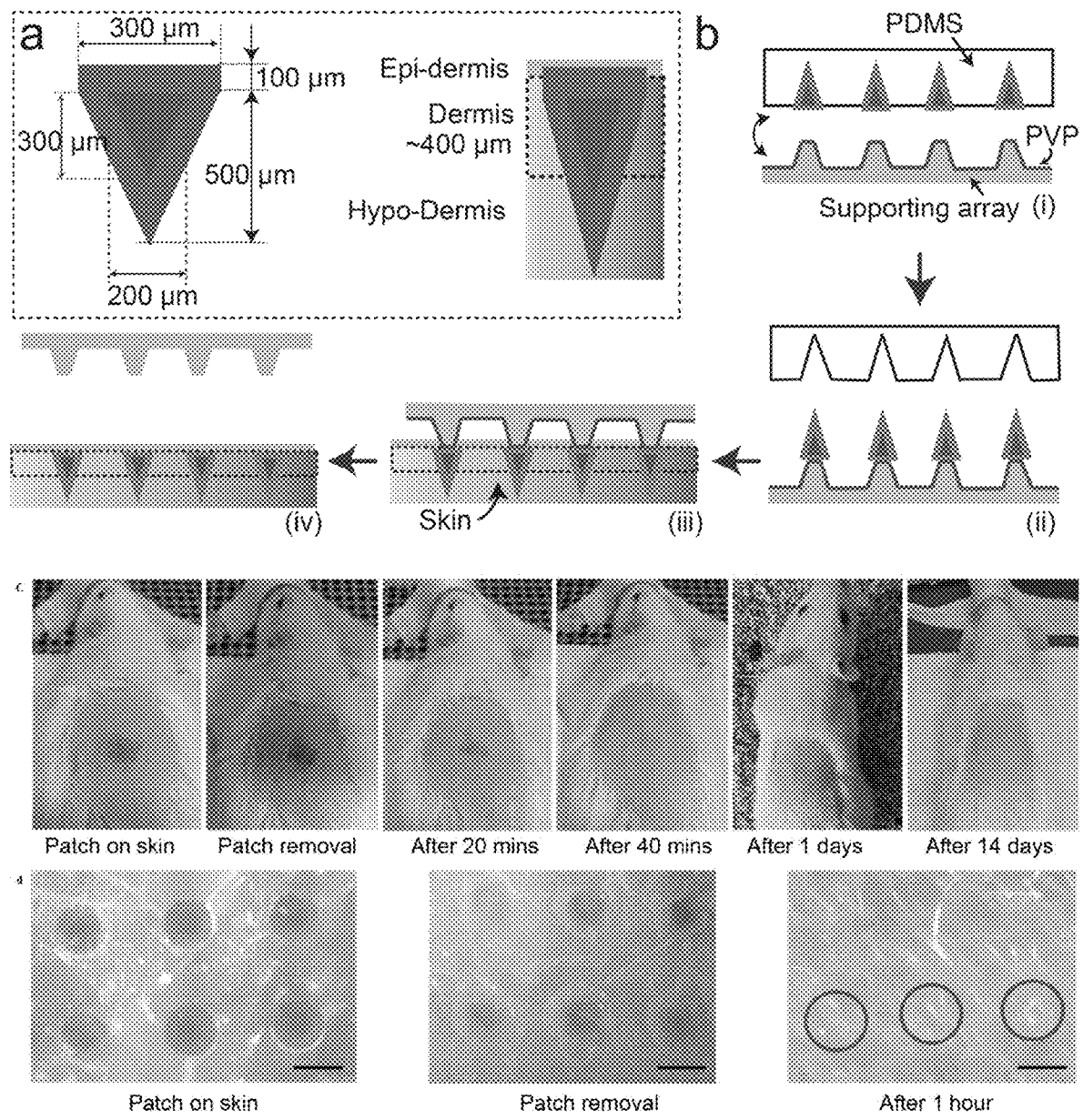
FIG. 4 illustrates a microneedle design and the use of supporting array to fully embed the needles into skin. Illustration showing exemplary dimensions of the microneedles (at a). Process to transfer microneedles onto a supporting array for insertion into skin (at b). Results (at c-d) show the fully-embedded microneedles inserted into rodent skin. The skin quickly heals after 60 minutes of implantation. The red circle shows the wound holes which are healed and closed up after 60 minutes of inserting/embedding the microneedles into the mice skin.

With reference to FIG. 4, in one embodiment, the drug core includes a maximum diameter of 200 µm and a height of 300 µm. This is short enough to allow the drug core to be situated inside the dermal layer of skin after insertion (FIG. 4 (at a, right)). The arrays made of PLA can be fabricated by micro-molding, without removal of the scum layer. PVP can be used to coat these arrays and selectively removed by water to release the drug microneedles into skin after insertion (FIG. 4 (at b, (iii)-(iv))). A PVP-coated PLA array is used as supporting arrays to fully implant the needles into skin. To bond the microneedles with the supporting array, the microneedles (trapped inside PDMS) can be aligned and brought into contact with the PLA supporting array and then a low heat can be applied for bonding (FIG. 4 (at b, (i)-(ii))). This process is again based on the SEAL method. As seen in FIG. 4 (at c), the fully-embedded microneedles are inserted into mice skin. The skin layer, after the needle insertion, could quickly heal to close up the opened wound/holes, as seen in FIG. 4 (at d).

Figure 5:
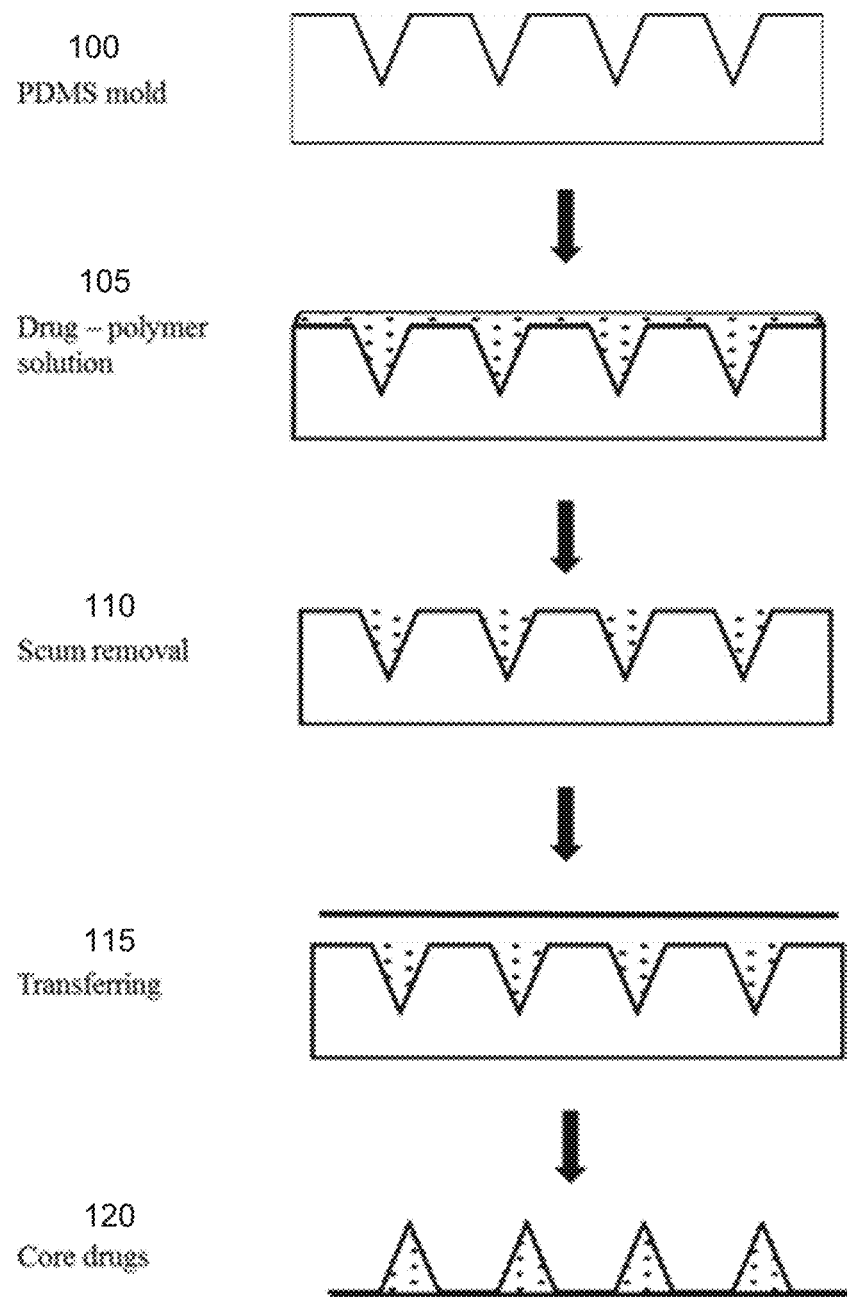
FIG. 5 illustrates a manufacturing process that generates a therapeutic agent assembly according to an embodiment of the invention.

With reference to FIG. 5, a manufacturing process that creates the drug delivery system according to an embodiment of the present disclosure is illustrated. In step 100, a non-adhesive negative mold (i.e., PDMS or Teflon, Polytetrafluoroethylene-PTFE or Perfluoropolyether-PFPE) is made by casting hydrophobic materials onto a master microneedles structure which is fabricated by photolithography or 3D printing or micro-machining etc. After the material is cured, it is peeled off from the master mold.

At step 105, to prepare the core-drugs, the therapeutic agents (e.g., drugs or vaccines such as Prevnar-13, HPV, IPV, insulin, growth hormone, pain medicine, allergic drugs, etc.) are dissolved or dispersed in suitable polymer solutions (i.e., water soluble polymer Poly(vinylpyrrolidone)—PVP or Poly(vinyl alcohol)—PVA).

Appropriate amounts of the solution or suspension are pipetted onto the prepared inverse mold as described above and left under vacuum to remove any air bubbles. Solvents are then allowed to evaporate. Lyophilization can be used to remove non-volatile organic solvents. Depending on the nature of solutions/suspensions, this step can be repeated several times and additional centrifugations can be applied until the mold is fully packed.

The above filling step usually results in a residual layer on the mold (scum layer). This scum layer is then removed as shown in step 110 by spinning accompanied with gently dropping of a suitable solvent (e.g., water, acetone, methanol, ethanol, dimethyl sulfoxide (DMSO)) on top of the mold. The chosen solvents should be able to dissolve the residual materials. The spinning speed depends on the viscosity of the materials and the architecture of the mold.

At step 115, the scum-free core-drugs are then transferred onto a sacrificial layer. The sacrificial layer can be a solid polymer film (i.e., PLGA) which is placed on top of the mold then compressed at its glass transition temperature under vacuum. Or, a concentrated polymer solution can be used as the sacrificial layer by pipetting onto the mold and allowing solvent to evaporate.

As shown in step 120, this whole structure is then delaminated onto a solid substrate, such as a glass slide, using heat-assisted micro-transfer molding. The fabricated core-drugs are used in a later loading step.

Figure 6:
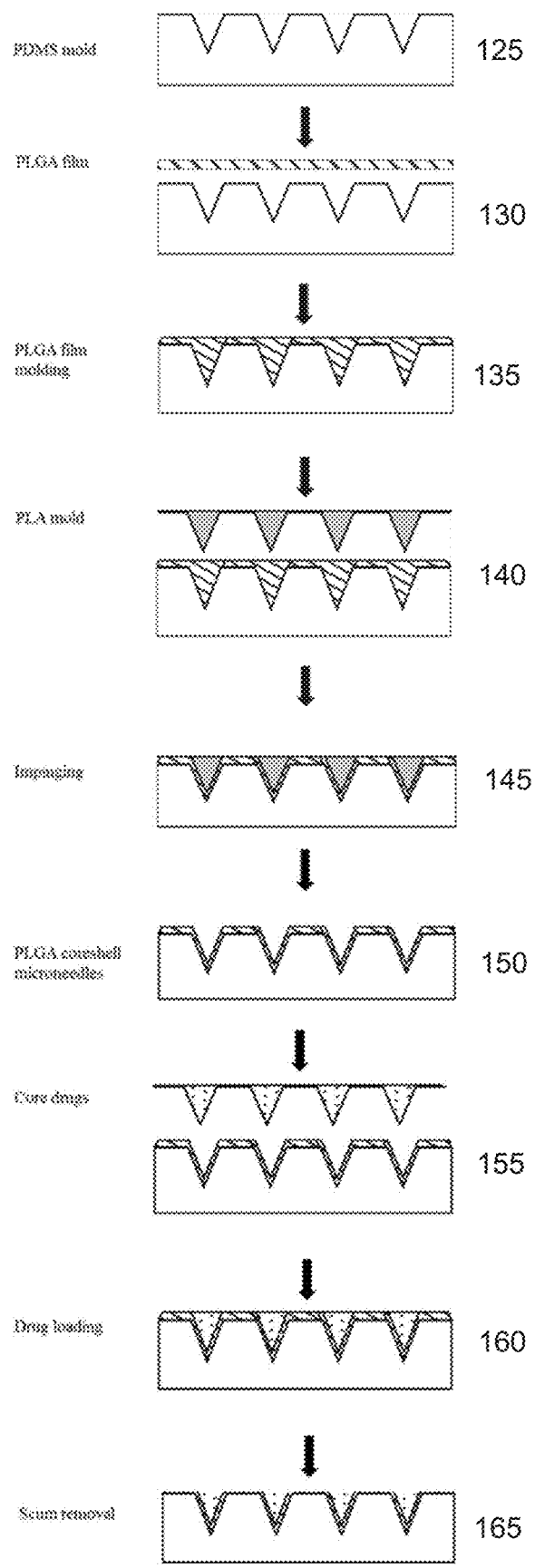
FIG. 6 illustrates a process of fabricating a core microneedle assembly and loading of a therapeutic agent according to an embodiment of the invention.

With reference to FIG. 6, a process of fabricating the coreshell microneedle and drug loading is illustrated. At step 125, a non-adhesive negative mold is made by casting hydrophobic materials (i.e., PDMS, Teflon, Polytetrafluoroethylene-PTFE, or Perfluoropolyether-PFPE) onto a master microneedles structure which is fabricated by photolithography, 3D printing, micro-machining, etc. After the material is cured, it is peeled off from the master mold.

A polymer film is then compression molded into the prepared mold at step 130 to form the microneedles. Typically, the polymer of interest such as PLGA is heat-pressed onto the mold at its melting or glass transition temperature under vacuum. The polymer fills the mold cavities at step 135.

To create the core structure, with reference to step 140, a positive mold which can be fabricated from polymers (e.g., PLA), metal, elastomers (PFPE), etc. is first prepared by compression molding, micro-machining, photolithography. Depending on the hydrophobicity of the materials, additional surface treatment can be applied to the mold in order to prevent adhesion in later manufacturing steps.

At step 145, this core structure or second mold which has smaller dimensions and the same relative spacing is aligned, using an alignment device, and then pressed into the microneedles (on the PDMS mold) which have been heated prior to this step. At an elevated temperature, the second mold will penetrate into the soft microneedles, creating dimple-like structures in the microneedles.

At step 150, after peeling off the second mold, the coreshell microneedles are obtained and trapped inside the first mold.

At step 155, the core-drugs are aligned using a similar device as above and loaded into the coreshell microneedles.

The residual scum layer is then removed at step 160 using the same method as described above. Suitable solvents are dropped onto the mold while spinning at high speed. At step 165, the scum-free coreshell microneedles are entrapped inside the mold.

Figure 7:
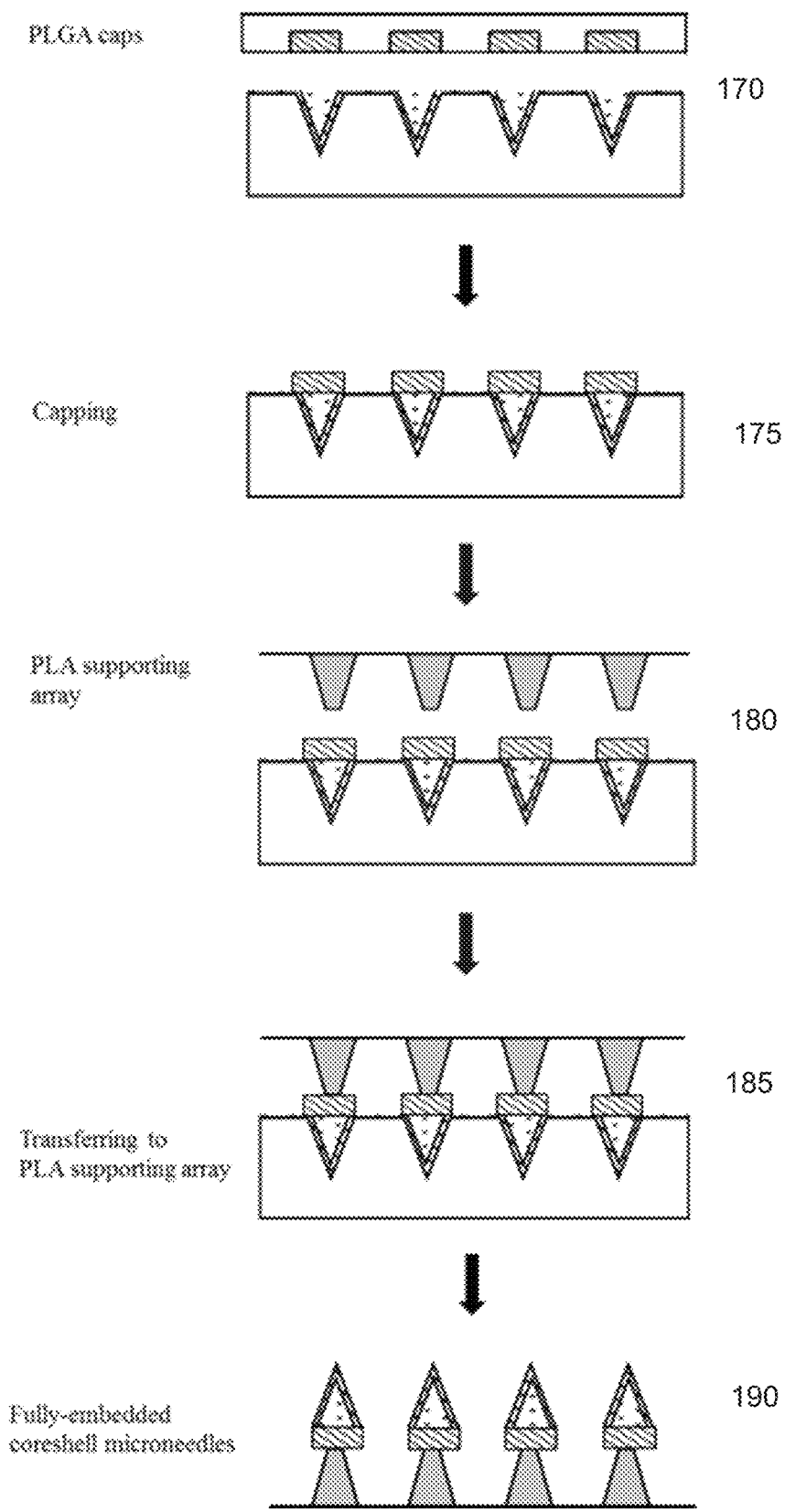
FIG. 7 illustrates a method for fabricating caps for the core microneedle assembly according to an embodiment of the invention.

With reference to FIG. 7, which is a continuation of FIG. 6, caps for the coreshell microneedles are fabricated by following similar procedures of compression molding and scum removal. In brief, another mold for the caps is made by a similar casting of hydrophobic materials on a master structure as described above. A polymer film such as PLGA is compression molded into the mold under heating and vacuum at step 170. Then the scum layer is removed leaving individual caps.

At step 175, the caps trapped inside the mold are aligned and placed on top of the fabricated coreshell microneedles from FIG. 6. With heat-assistance, the caps are bonded with the coreshell microneedles base. The mold is then peeled off.

In the next step, step 180, the coreshell microneedles are transferred onto a supporting array. This array can be manufactured by several microfabrication methods like compression molding, micro-machining, or photolithography.

The array is then coated at step 185 with a water soluble polymer (i.e., PVP, PVA). Then, it is aligned with the coreshell microneedles, contact between them is made, and sufficient heat for bonding with the PLGA caps is supplied.

The mold entrapping the coreshell microneedles is then peeled off at step 190 leaving a free standing coreshell microneedle assembly on the supporting array which can be fully-embedded into the skin.

The drug delivery system may include a computer processor in electronic communication with the coreshell microneedle assembly. The computer processor is programmed with computer readable instructions to initiate active release of the therapeutic agent either as a one-time release or as a plurality of pre-programmed timed releases of the therapeutic agent. The computer processor can be in electronic communication with an actuator (e.g., piezoelectric (mechanical) pump, electromagnetic pump, or electrical pump can be integrated into the microneedle patch) to initiate the release of the therapeutic agent into the skin based on the programmed instructions.

Various features and advantages of the invention are set forth in the following claims.

What is claimed is:

1. A method of manufacturing a microneedle assembly, the method comprising:
   generating a core microneedle assembly by:
      filling a plurality of microneedle cavities in a first silicone mold with a copolymer, and
      generating a core from the copolymer in each of the copolymer-filled cavities;
   generating a therapeutic agent assembly by:
      filling a plurality of cavities in a second silicone mold with a therapeutic agent,
      spinning the second silicone mold to remove a scum layer of the therapeutic agent on the second silicone mold, and
      removing molded portions of the therapeutic agent from the cavities of the second mold and transferring the molded portions of the molded therapeutic agent to a substrate;
   aligning the therapeutic agent assembly with the core microneedle assembly to thereby fill cavities of the cores in the core microneedle assembly with respective ones of the molded portions of the therapeutic agent; and
   spinning the first silicone mold having the molded portions of the therapeutic agent filled into the core cavities to remove a scum layer of the copolymer on the first silicone mold.

2. The method of claim 1, wherein the cavities in each of the first silicone mold and the second silicone mold are conical shaped.

3. The method of claim 1, wherein the copolymer is Poly(D,L-lactide-co-glycolide) (PLGA).

4. The method of claim 1, further comprising generating the first silicone mold by pouring and then curing polydimethylsiloxane (PDMS) over a master structure.

5. The method of claim 1, further comprising dropping a solvent on the scum layer of the copolymer to remove the scum layer of the copolymer during said spinning of the first silicone mold.

6. The method of claim 5, wherein the solvent is acetone.

7. The method of claim 1, further comprising dropping water on the scum layer of the therapeutic agent to remove the scum layer of the therapeutic agent during said spinning the second silicone mold.

8. The method of claim 1, wherein the therapeutic agent is mixed with a polymeric carrier of biocompatible or biodegradable polymers.

9. The method of claim 8, wherein the polymeric carrier is Polyvinylpyrrolidone (PVP).

10. The method of claim 1, further comprising generating a cap assembly by:
   filling a plurality of cavities in a third silicone mold with a copolymer to form a plurality of caps,
   spinning the third silicone mold to remove a scum layer of the copolymer on the third silicone mold,
   removing the molded caps from the third mold and transferring the molded caps onto the core microneedle assembly, and aligning the cap assembly with the core microneedle assembly to thereby cover the cores in the core microneedle assembly with the caps.

11. The method of claim 10, further comprising applying heat to bond the cap assembly to the core microneedle assembly.

12. The method of claim 10, further comprising coating a supporting array with a water soluble polymer and contacting the supporting array with the cap assembly.

13. The method of claim 12, further comprising applying heat to bond the supporting array to the cap assembly for removing the microneedle assembly from the first silicone mold.

* * * * *